(12) United States Patent
Fang et al.

(10) Patent No.: US 11,369,302 B2
(45) Date of Patent: Jun. 28, 2022

(54) IMPLANTABLE FLEXIBLE NEURAL MICROELECTRODE COMB, AND PREPARATION METHOD AND IMPLANTATION METHOD THEREFOR

(71) Applicant: NATIONAL CENTER FOR NANOSCIENCE AND TECHNOLOGY, CHINA, Beijing (CN)

(72) Inventors: Ying Fang, Beijing (CN); Jinfen Wang, Beijing (CN); Shouliang Guan, Beijing (CN); Mingde Du, Beijing (CN); Liang Zou, Beijing (CN)

(73) Assignee: National Center for Nanoscience and Technology, China, Beijing (CN)

( * ) Notice: Subject to any disclaimer, the term of this patent is extended or adjusted under 35 U.S.C. 154(b) by 404 days.

(21) Appl. No.: 16/471,545

(22) PCT Filed: Feb. 6, 2017

(86) PCT No.: PCT/CN2017/072937
§ 371 (c)(1),
(2) Date: Jun. 19, 2019

(87) PCT Pub. No.: WO2018/113073
PCT Pub. Date: Jun. 28, 2018

(65) Prior Publication Data
US 2019/0313933 A1    Oct. 17, 2019

(30) Foreign Application Priority Data
Dec. 20, 2016   (CN) .......................... 201611183487.7

(51) Int. Cl.
*H01K 3/02*    (2006.01)
*A61B 5/291*   (2021.01)
(Continued)

(52) U.S. Cl.
CPC ................ *A61B 5/291* (2021.01); *A61B 5/24* (2021.01); *H05K 1/028* (2013.01); *H05K 1/09* (2013.01);
(Continued)

(58) Field of Classification Search
CPC .......... H05K 1/028; H05K 1/09; H05K 1/118; H05K 3/0023; H05K 3/14; H05K 3/28;
(Continued)

(56) References Cited

U.S. PATENT DOCUMENTS 6,993,392 B2 *   1/2006   Nicolelis .............. A61N 1/0529
                                                        600/377
9,861,288 B2 *   1/2018   Ma .......................... A61B 5/291

FOREIGN PATENT DOCUMENTS

CN    101912666 A    12/2010
CN    102544052 A    7/2012
(Continued)

OTHER PUBLICATIONS

PCT/CN2017/072937 International Search Report dated Aug. 8, 2017.

*Primary Examiner* — Donghai D Nguyen
(74) *Attorney, Agent, or Firm* — Venable LLP; Henry J. Daley

(57) ABSTRACT

Disclosed are an implantable flexible neural microelectrode comb, and a preparation method and implantation method therefor. The flexible neural microelectrode comb is mainly composed of a flexible substrate layer (1), a flexible insulation layer (2), and a metal connection wire layer (3) arranged between the flexible substrate layer (1) and the flexible insulation layer (2); the flexible neural microelectrode comb comprises a filament structure (4), a mesh structure (5), a plane structure (6) and a bonding pad area (7) connected in sequence; electrode sites (8) are arranged on (Continued)

the filament structure (4); bonding pads are arranged on the bonding pad area (7); the metal connection wire layer (3) is composed of metal connection wires connecting the electrode sites (8) and the bonding pads; and the flexible insulation layer (2) is not arranged on the surfaces of the electrode sites (8) and the bonding pads. The prepared flexible neural microelectrode comb has a structure gradually changing from a filament to a mesh to a plane structure, thus improving mechanical stability during a deformation process. The mechanical properties of the implantable flexible neural microelectrode comb match brain tissue, the implantation footprint is small, an inflammatory response of the brain is avoided, and electrophysiological signals in the brain can be stably tracked and measured in a multi-site manner for a long time.

17 Claims, 4 Drawing Sheets

(51) Int. Cl.
| | | |
|---|---|---|
| | *H05K 1/02* | (2006.01) |
| | *H05K 1/09* | (2006.01) |
| | *H05K 1/11* | (2006.01) |
| | *H05K 3/00* | (2006.01) |
| | *H05K 3/14* | (2006.01) |
| | *H05K 3/28* | (2006.01) |
| | *A61B 5/24* | (2021.01) |

(52) U.S. Cl.
CPC ........... *H05K 1/118* (2013.01); *H05K 3/0023* (2013.01); *H05K 3/14* (2013.01); *H05K 3/28* (2013.01); *A61B 2562/0209* (2013.01); *A61B 2562/125* (2013.01); *A61B 2562/164* (2013.01); *H05K 2201/09681* (2013.01)

(58) Field of Classification Search
CPC .............. A61B 5/24; A61B 2562/0209; A61B 2562/125; A61B 2562/028; Y10T 29/49222; A61N 1/0529
USPC .................... 29/825, 846, 874, 884; 600/377
See application file for complete search history.

(56) References Cited

FOREIGN PATENT DOCUMENTS

| | | |
|---|---|---|
| CN | 106178271 A | 12/2016 |
| KR | 20150038895 A | 4/2015 |

\* cited by examiner

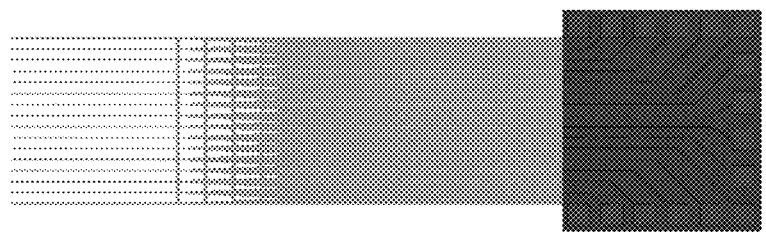
Fig. 6
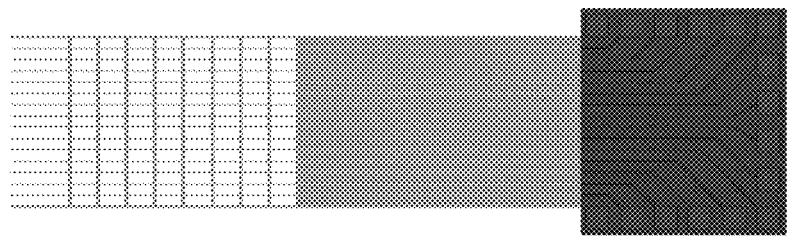
Fig. 7
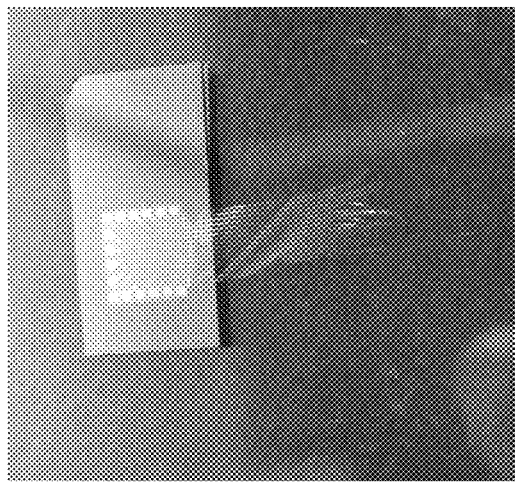 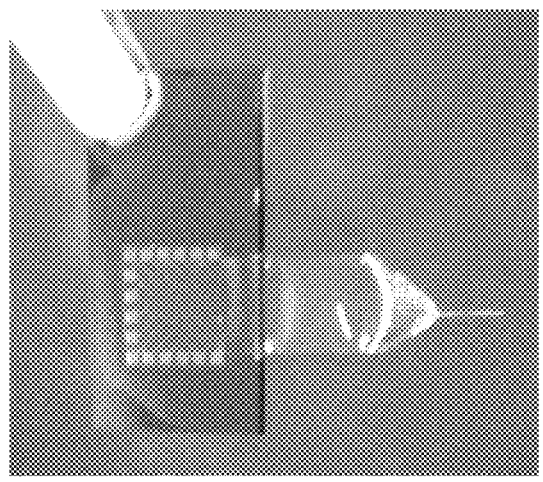
Fig. 8(a)  Fig. 8(b)

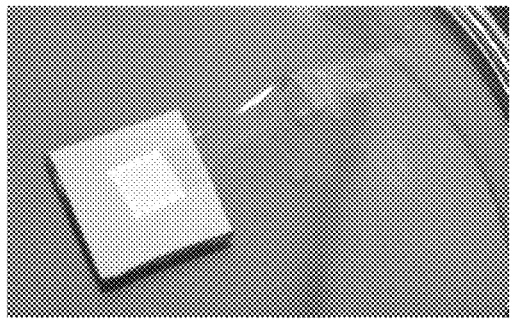 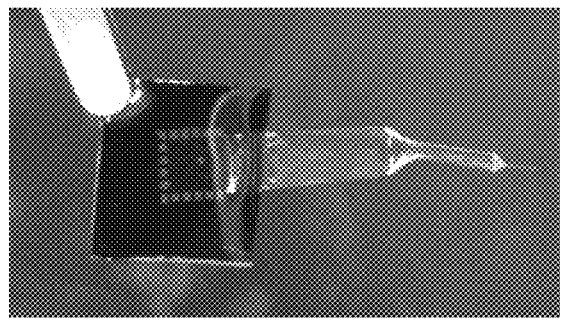
Fig. 9(a)  Fig. 9(b)
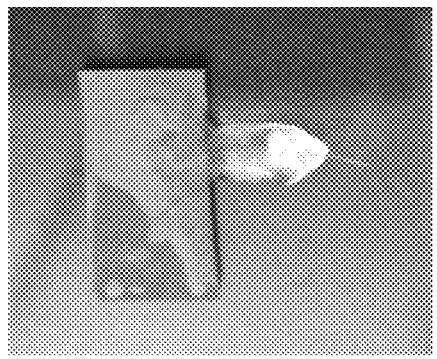 
Fig. 10(a)  Fig. 10(b)
Fig. 11

IMPLANTABLE FLEXIBLE NEURAL MICROELECTRODE COMB, AND PREPARATION METHOD AND IMPLANTATION METHOD THEREFOR

TECHNICAL FIELD

The present invention belongs to the technical fields of neural biomaterials and microelectronics, relates to a flexible comb-shaped neural microelectrode, and a preparation method and implantation method therefor, and in particular to an implantable flexible comb-shaped neural microelectrode, and a preparation method and implantation method therefor.

BACKGROUND

Neural microelectrode is a key component interfacing neural tissue and external devices, and has broad applications in the treatment of neurological diseases and the study of cognitive behaviors. The quality of the neural microelectrode directly determines the ultimate performance of the neural activity recording systems and the neuroprosthetics systems. An ideal implantable neural electrode should meet the following characteristics: the smallest possible implantation tissue damage, effective recording and stimulation capabilities, good biocompatibility, and long-term stability.

At present, the most widely applied implantable neural microelectrodes are silicon-based rigid neural microelectrodes. The mechanical mismatch between the rigid neural microelectrodes and neural tissues causes micromotion at their interfaces, leading to inflammatory response of the brain; moreover, glial scar formation around the rigid neural microelectrodes eventually leads to electrode failure. Compared to rigid neural microelectrodes, flexible neural microelectrodes can form tight interfaces with neural tissue and move with the brain tissue, leading to reduced inflammatory response. Therefore, it is essential to develop implantable flexible neural microelectrodes with comparable mechanical properties to brain tissue.

Flexible neural microelectrode with comparable mechanical properties to brain tissue is not stiff enough to penetrate the brain tissue by itself. Therefore, it is necessary to develop implantation methods for ultrathin flexible neural electrodes into brain tissue. On the other hand, it is important to reduce the implantation footprint of the neural electrodes and thus the brain tissue damage from the implantation, and to simultaneously provide multiple recording electrode sites at the same time.

SUMMARY

To solve the above problems in the prior art, the present invention provides an implantable flexible comb-shaped neural microelectrode, and a preparation method and implantation method therefor. The present invention prepares a flexible comb-shaped neural microelectrode by using flexible materials with good biocompatibility as the substrate layer and the insulation layer; the front end of the flexible comb-shaped neural microelectrode consists of a row of microelectrode filaments that are connected to a mesh structure and then a plane structure; the microelectrode filaments are electrically connected to the bonding pads at the back end. The microelectrode filaments at the front end can detect neural activity signals, and the filament-mesh-plane design can improve the mechanical stability of the flexible comb-shaped neural microelectrode during deformation. The implantable comb-shaped neural microelectrode can self-assemble into a needle-like structure under the surface tension force of a liquid, thereby greatly reducing its implantation footprint in brain tissue. The mechanical properties of the flexible comb-shaped neural microelectrode is compatible with that of the brain tissue, which can allow multi-site and long-term stable recording of neural activity signals in brain.

To achieve this purpose, the present invention adopts the following technical solutions:

In the first aspect, the present invention provides an implantable flexible comb-shaped neural microelectrode mainly consisting of a flexible substrate layer, a flexible insulation layer, and a metal connection wire layer arranged between the flexible substrate layer and the flexible insulation layer.

The flexible comb-shaped neural microelectrode comprises a filament structure, a mesh structure, a plane structure, and a bonding pad area that are sequentially connected; the electrode sites are arranged on the filament structure; and the bonding pads are arranged on the bonding pad area.

The metal connection wire layer consists of metal connection wires connecting the electrode sites and the bonding pads.

There is no flexible insulation layer on the electrode sites and the bonding pads, while the metal connection wires that connect the electrode sites and the bonding sites are covered by the flexible insulation layer.

In the present invention, the flexible substrate layer, the flexible insulation layer, and the metal connection wire layer arranged between the flexible substrate layer and the flexible insulation layer form a sandwiched structure.

The implantable flexible comb-shaped neural microelectrode of the present invention has a unique filament-mesh-plane transition structure, and the filaments can float on water; the filaments can self-assemble into a needle-like structure under the liquid capillary force when withdrawn into air from liquid, which facilitates the implantation of the comb-shaped neural microelectrode after solidification; the mesh structure forms a series of puffs or semi-puffs under the liquid capillary force, and can form conformal contact with the brain after implantation.

The following technical solutions are preferred ones of the present invention, but should not be construed as a limitation on the implementation of technical solutions provided by the present invention, and the technical objects and advantageous effects of the present invention can be better achieved and realized by the following technical solutions.

As a preferred technical solution of the present invention, an adhesive layer is arranged between the flexible substrate layer and the metal connection wire layer.

Preferably, the adhesion layer is made of chromium.

Preferably, the adhesion layer has a thickness of 1 nm to 100 nm, e.g., 1 nm, 5 nm, 10 nm, 20 nm, 30 nm, 40 nm, 50 nm, 60 nm, 70 nm, 80 nm, 90 nm or 100 nm, and the like, but not limited to the enumerated values recited herein, with the unenumerated ones within the numerical range being also applicable, preferably 5 nm.

Preferably, the flexible substrate layer is made of any one selected from the group consisting of SU-8 photoresist, parylene, and polyimide, or a combination of at least two selected therefrom. Typical but non-limiting examples of the combination include: a combination of SU-8 photoresist and parylene, a combination of parylene and polyimide, a combination of SU-8 photoresist, parylene, and polyimide, and the like.

Preferably, the flexible substrate layer has a thickness of 1 μm to 20 μm, e.g., 1 μm, 2 μm, 3 μm, 4 μm, 5 μm, 10 μm, 13 μm, 15 μm, 17 μm, 20 μm, and the like, but not limited to the enumerated values recited herein, with the unenumerated ones within the numerical range being also applicable, preferably 5 μm.

Preferably, the flexible insulation layer is made of any one selected from the group consisting of SU-8 photoresist, parylene, and polyimide, or a combination of at least two selected therefrom. Typical but non-limiting examples of the combination include: a combination of SU-8 photoresist and parylene, a combination of parylene and polyimide, a combination of SU-8 photoresist, parylene, and polyimide, and the like.

Preferably, the flexible insulation layer has a thickness of 1 μm to 20 μm, e.g., 1 μm, 2 μm, 3 μm, 4 μm, 5 μm, 10 μm, 13 μm, 15 μm, 17 μm, 20 μm, and the like, but not limited to the enumerated values recited herein, with the unenumerated ones within the numerical range being also applicable, preferably 5 μm.

In the present invention, both the flexible substrate layer and the flexible insulation layer are made of a flexible material with good biocompatibility and mechanical flexibility.

Preferably, the metal connection wires in the metal connection wire layer are made of any one material selected from the group consisting of gold, platinum, and iridium, or a combination of at least two selected therefrom. Typical but non-limiting examples of the combination include: a combination of gold and platinum, a combination of platinum and iridium, a combination of gold, platinum, and iridium, and the like. The material for making the metal connection wires is not limited to gold, platinum or iridium, other metallic materials that can achieve the same conductive properties are also applicable to the present invention.

Preferably, the metal connection wire layer has a thickness of 10 nm to 1000 nm, e.g., 10 nm, 50 nm, 100 nm, 300 nm, 500 nm, 800 nm, 1000 nm, and the like, but not limited to the enumerated values recited herein, with the unenumerated ones within the numerical range being also applicable, preferably 100 nm.

Preferably, the metal connection wires in the metal connection wire layer have a wire width of 1 μm to 50 μm, e.g., 1 μm, 5 μm, 10 μm, 20 μm, 30 μm, 40 μm, 50 μm, and the like, but not limited to the enumerated values recited herein, with the unenumerated ones within the numerical range being also applicable, preferably 10 μm.

As a preferred technical solution in the present invention, the number of filaments of the filament structure is 1 to 1000, e.g., 1, 10, 50, 100, 300, 500, 700, 1000, and the like, but not limited to the enumerated values recited herein, with the unenumerated ones within the numerical range being also applicable, preferably 16.

Preferably, the electrode sites are arranged on each filament of the filament structure.

Preferably, the number of the electrode sites on the filament structure is 1 to 1000, e.g., 1, 10, 50, 100, 300, 500, 700, 1000, and the like, but not limited to the enumerated values recited herein, with the unenumerated ones within the numerical range being also applicable, preferably 16.

In the present invention, the electrode sites are used for stimulating or recording of neural electrophysiological signals. These electrode sites form an electrode array, each array has one or more neural electrode sites arranged linearly or spaced apart on the filaments at the front end (as shown in FIG. 3 (*a*) and FIG. 3 (*b*)).

Preferably, the electrode sites comprise electrode substrates and electrodes located at the center of the electrode substrates.

Preferably, the electrode substrates are circular having a diameter of 1 μm to 200 μm, e.g., 1 μm, 10 μm, 30 μm, 40 μm, 50 μm, 100 μm, 130 μm, 150 μm, 170 μm, 200 μm, and the like, but not limited to the enumerated values recited herein, with the unenumerated ones within the numerical range being also applicable, preferably 40 μm.

Preferably, the electrodes are circular having a diameter of 1 μm to 100 μm, e.g., 1 μm, 5 μm, 10 μm, 30 μm, 50 μm, 70 μm, 100 μm, and the like, but not limited to the enumerated values recited herein, with the unenumerated ones within the numerical range being also applicable, preferably 20 μm.

As a preferred technical solution in the present invention, the overall length of the filament structure, the mesh structure, and the plane structure in the implantable flexible comb-shaped neural microelectrode is 1 mm to 5 cm, e.g., 1 mm, 5 mm, 1 cm, 2 cm, 3 cm, 4 cm, 5 cm, and the like, but not limited to the enumerated values recited herein, with the unenumerated ones within the numerical range being also applicable, preferably 1 cm or 2 cm.

In the present invention, the size of the flexible comb-shaped neural microelectrode can be adjusted according to the requirements of practical applications to meet the detection requirements of different animal brains, and is not limited to the sizes listed above.

Preferably, the filament structure has a length of 1 mm to 5 cm, e.g., 1 mm, 3 mm, 5 mm, 1 cm, 2 cm, 3 cm, 4 cm, 5 cm, and the like, but not limited to the enumerated values recited herein, with the unenumerated ones within the numerical range being also applicable, preferably 1 mm, 3 mm, or 5 mm.

In the present invention, the filament structure of the flexible comb-shaped neural microelectrode can form microneedles with various lengths.

Preferably, each filament in the filament structure has a width of 1 μm to 200 μm, e.g., 1 μm, 10 μm, 20 μm, 50 μm, 100 μm, 150 μm, 200 μm, and the like, but not limited to the enumerated values recited herein, with the unenumerated ones within the numerical range being also applicable, preferably 20 μm.

Preferably, the plane structure has a length of 1 mm to 1 cm, e.g., 1 mm, 3 mm, 5 mm, 7 mm, 1 cm, and the like, but not limited to the enumerated values recited herein, with the unenumerated ones within the numerical range being also applicable; and it has a width of 1 mm to 5 cm, e.g., 1 mm, 3 mm, 5 mm, 7 mm, 1 cm, 2 cm, 3 cm, 4 cm, 5 cm, and the like, but not limited to the enumerated values recited herein, with the unenumerated ones within the numerical range being also applicable.

Preferably, the size of the mesh structure varies with that of the filament structure.

Preferably, the longitudinal support strips in the mesh structure have a width of 1 μm to 100 μm, e.g., 1 μm, 10 μm, 20 μm, 30 μm, 40 μm, 50 μm, 60 μm, 70 μm, 80 μm, 90 μm, 100 μm, and the like, but not limited to the enumerated values recited herein, with the unenumerated ones within the numerical range being also applicable, preferably 50 μm.

Preferably, the bonding pad area has a size of (0.1-4) mm×(0.1-4) mm, e.g., 0.1 mm×0.1 mm, 0.2 mm×0.1 mm, 1 mm×2 mm, 3.5 mm×3.5 mm, 3.7 mm×4 mm, 4 mm×4 mm, 4 mm×3.7 mm, and the like, but not limited to the enumerated values recited herein, with the unenumerated ones within the numerical range being also applicable.

Preferably, the bonding pads on the bonding pad area have a size of (100-2000) μm×(100-2000) e.g., 100 μm×100 μm, 200 μm×100 μm, 300 μm×400 μm, 400 μm×400 μm, 600 μm×800 μm, 1000 μm×1000 μm, 1300 μm×1500 μm, 1500 μm×1700 μm, 2000 μm×2000 μm and the like, but not limited to the enumerated values recited herein, with the unenumerated ones within the numerical range being also applicable, preferably 400 μm×400 μm.

As a preferred technical solution in the present invention, the mesh structure is any one selected from the group consisting of a longitudinally changing mesh structure, a transversely changing mesh structure, a uniform mesh structure, and a mesh structure with a longitudinal angle of 45 degrees, or a combination of at least two selected therefrom.

In the present invention, the longitudinal angle refers to an angle at which the longitudinal support strip deviates from the orthogonal direction.

Preferably, the longitudinally changing mesh structure comprises transverse mesh strips and longitudinal support strips, and the distances between the adjacent longitudinal support strips increase gradually (as shown in FIG. 5).

Preferably, the longitudinally changing mesh structure comprises transverse mesh strips and longitudinal support strips, and the distances between the adjacent longitudinal support strips increase gradually toward the side of the filament structure.

Preferably, the distances between the longitudinal support strips increase gradually from 1 μm to 100 μm, e.g., 1 μm, 5 μm, 10 μm, 30 μm, 50 μm, 70 μm, 100 μm, and the like, but not limited to the enumerated values recited herein, with the unenumerated ones within the numerical range being also applicable, preferably 10 μm.

Preferably, the transversely changing mesh structure comprises transverse mesh strips and longitudinal support strips, and the widths of the transverse mesh strips gradually decrease from the plane structure to the filament structure (as shown in FIG. 6).

Preferably, the transversely changing mesh structure comprises transverse mesh strips and longitudinal support strips, and the widths of the transverse mesh strips gradually decrease to 1 μm~200 μm, e.g., 1 μm, 5 μm, 10 μm, 30 μm, 50 μm, 70 μm, 100 μm, 130 μm, 150 μm, 170 μm, 200 μm, and the like, but not limited to the enumerated values recited herein, with the unenumerated ones within the numerical range being also applicable, preferably 10 μm or 30 μm.

Preferably, the uniform mesh structure comprises transverse mesh strips and longitudinal support strips, and the distances between the adjacent longitudinal support strips are equal (as shown in FIG. 7) and are 10 μm to 1000 μm, e.g., 10 μm, 30 μm, 50 μm, 70 μm, 100 μm, 300 μm, 500 μm, 700 μm, 1000 μm, and the like, but not limited to the enumerated values recited herein, with the unenumerated ones within the numerical range being also applicable, preferably 500 μm.

Preferably, the uniform mesh structure comprises transverse mesh strips and longitudinal support strips, and the distances between the adjacent transverse mesh strips are equal and are 10 μm to 1000 μm, e.g., 10 μm, 30 μm, 50 μm, 70 μm, 100 μm, 300 μm, 500 μm, 700 μm, 1000 μm, and the like, but not limited to the enumerated values recited herein, with the unenumerated ones within the numerical range being also applicable, preferably 200 μm.

In a second aspect, the present invention provides a preparation method of the aforementioned implantable flexible comb-shaped neural microelectrode, comprising the following steps:

(1) spin-coating a positive photoresist on a carrier, prebaking, photolithography, leaving the bonding pad area protected by a photoresist, post-exposure baking to harden, and then removing the exposed photoresist;

(2) evaporating or sputtering a sacrificial layer on the carrier obtained after the treatment of step (1), and forming a sacrificial layer and a marker pattern after a lift-off process;

(3) spin-coating a flexible substrate material on the side of the carrier where the sacrificial layer and the marker pattern are formed in step (2), sequentially prebaking, exposing, post-exposure baking, and developing to form a flexible substrate layer, and hardening at a high temperature of 180° C.;

(4) spin-coating a positive photoresist on the flexible substrate layer formed in step (3), prebaking, exposing, and developing to form patterned electrode sites, connection wires, and bonding pads, and then forming an adhesive layer by electron beam or thermal evaporation;

(5) forming a metal layer by electron beam or thermal evaporation on the adhesive layer formed in step (4), and then producing the electrode sites, connection wires, and bonding pads after a lift-off process;

(6) spin-coating a flexible insulation material on the metal layer where the electrode sites, connection wires, and bonding pads are formed in step (5), prebaking, exposing, post-exposure baking, and developing to expose the electrode sites and the bonding pads, and hardening at a high temperature of 180° C.;

(7) placing the flexible comb-shaped microelectrode obtained in step (6) in a sacrificial layer removing solution, and releasing the flexible comb-shaped microelectrode;

(8) cutting the flexible comb-shaped microelectrode fabricated in step (7) to obtain a final product.

The processes, such as spin coating, prebaking, photolithography, post-exposure baking and hardening, removing the exposed photoresist, electron beam or thermal evaporation, and lift-off, as described in the above steps, are conventional technical means in the micro-nano fabrication field, so the specific operation processes will not be described herein.

As a preferred technical solution in the present invention, the carrier on which the positive photoresist is spin-coated in step (1) is pretreated.

Preferably, the pretreatment consists of: washing the carrier with acetone and water, oven drying, and then cleaning with oxygen plasma. Wherein, the purpose of drying is to remove moisture on the surface of the carrier.

Preferably, the carrier is a silicon wafer and/or a glass substrate.

Preferably, the positive photoresist in step (1) is a S1813 and/or AZ1500 positive photoresist.

Preferably, the removal of the residual photoresist in step (1) is performed by using an oxygen plasma process.

As a preferred technical solution in the present invention, the sacrificial layer in step (2) has a thickness of 10 nm to 1000 nm, e.g., 10 nm, 30 nm, 50 nm, 70 nm, 100 nm, 300 nm, 500 nm, 700 nm, 1000 nm, and the like, but not limited to the enumerated values recited herein, with the unenumerated ones within the numerical range being also applicable, preferably 100 nm.

Preferably, the sacrificial layer in step (2) is an aluminum layer and/or a nickel layer.

Preferably, the flexible substrate material in step (3) is any one selected from the group consisting of SU-8 photoresist, parylene, and polyimide, or a combination of at least two selected therefrom. Typical but non-limiting examples of the combination include: a combination of SU-8 photoresist and parylene, a combination of parylene and polyimide, a combination of SU-8 photoresist, parylene and polyimide, and the like.

Preferably, the flexible substrate layer in step (3) has a thickness of 1 µm to 20 µm, e.g., 1 µm, 2 µm, 3 µm, 4 µm, 5 µm, 10 µm, 15 µm, 20 µm, and the like, but not limited to the enumerated values recited herein, with the unenumerated ones within the numerical range being also applicable, preferably 5 µm.

Preferably, the positive photoresist in step (4) is a S1813 and/or AZ1500 positive photoresist.

Preferably, the adhesive layer in step (4) is a chromium layer.

Preferably, the adhesion layer in step (4) has a thickness of 1 nm to 100 nm, e.g., 1 nm, 5 nm, 10 nm, 30 nm, 50 nm, 70 nm, 100 nm, and the like, but not limited to the enumerated values recited herein, with the unenumerated ones within the numerical range being also applicable, preferably 5 nm.

Preferably, the metal layer in step (5) is made of any one selected from the group consisting of gold, platinum, and iridium, or a combination of at least two selected therefrom. Typical but non-limiting examples of the combination include: a combination of gold and platinum, a combination of platinum and iridium, a combination of gold, platinum, and iridium, and the like. The material for making the metal connection wires is not limited to gold, platinum, or iridium, other metals that can achieve the same conductive properties are also applicable to the present invention.

Preferably, the metal layer in step (5) has a thickness of 10 nm to 1000 nm, e.g., 10 nm, 50 nm, 100 nm, 300 nm, 500 nm, 800 nm, 1000 nm, and the like, but not limited to the enumerated values recited herein, with the unenumerated ones within the numerical range being also applicable, preferably 100 nm.

Preferably, the flexible insulation material in step (6) is any one selected from the group consisting of SU-8 photoresist, parylene, and polyimide, or a combination of at least two selected therefrom.

Typical but non-limiting examples of the combination include: a combination of SU-8 photoresist and parylene, a combination of parylene and polyimide, a combination of SU-8 photoresist, parylene, and polyimide, and the like.

Preferably, the flexible insulation layer in step (6) has a thickness of 1 µm to 20 µm, e.g., 1 µm, 2 µm, 3 µm, 4 µm, 5 µm, 10 µm, 15 µm, 20 µm, and the like, but not limited to the enumerated values recited herein, with the unenumerated ones within the numerical range being also applicable, preferably 5 µm.

Preferably, the removal of sacrificial layer in step (7) consists of: etching the sacrificial layer.

Preferably, the etching process adopts a ferric trichloride and/or hydrochloric acid solution.

In a third aspect, the present invention provides an implantation method of the aforementioned implantable flexible comb-shaped neural microelectrode, comprising the following steps:
(1) the filaments of the flexible comb-shaped neural microelectrode spontaneously form a needle-like structure under the surface tension force of a liquid (such as water);
(2) solidifying the flexible comb-shaped neural microelectrode in step (1) with a solidifying material;
(3) solidifying the interface between the solidified flexible comb-shaped neural microelectrode and the carrier with an epoxy resin glue;
(4) inserting the flexible comb-shaped neural microelectrode as treated in step (2) into a biological tissue, washing the portion not implanted in the biological tissue to complete the implantation process.

In the present invention, once the flexible comb-shaped neural microelectrode is inserted into the biological tissue, the solidifying material will be exposed to a liquid and then be dissolved.

As a preferred technical solution in the present invention, the solidifying material in step (2) is polyethylene glycol.

The solidifying material used in the present invention is a material which is dissolvable or biodegradable in an organism, of which the stiffness after solidifying can meet the implantation requirements of the flexible electrode. At the same time, due to the good biocompatibility of the solidifying material, it causes no immune response in the brain; and the solidified material has good water solubility, and can decompose and release the flexible electrode in brain tissue.

Preferably, the polyethylene glycol has a molecular weight of 1000 to 4000, e.g., 1000, 1500, 2000, 2500, 3000, 3500, 4000, and the like, but not limited to the enumerated values recited herein, with the unenumerated ones within the numerical range being also applicable, preferably 2000.

Preferably, the solidifying in step (2) consists of: coating the molten solidifying material on the flexible comb-shaped neural microelectrode for solidifying.

Preferably, the washing in step (4) consists of: washing with an artificial cerebrospinal fluid.

In the present invention, the purpose of solidifying the flexible comb-shaped neural microelectrode is to improve the stiffness of the flexible comb-shaped neural microelectrode; while the purpose of solidifying the interface between the solidified flexible comb-shaped neural microelectrode and the carrier with an epoxy resin glue is to avoid fracture at the interface between the solidified flexible comb-shaped neural microelectrode and a silicon substrate.

As compared to the existing technologies, the present invention has the following beneficial effects:
(1) in contrast to conventional two-dimensional planar neural electrodes, the implantable flexible comb-shaped neural microelectrode of the present invention has electrode sites on each filament of the filament structure thereof, and these electrode sites make up an electrode array, wherein each filament can move freely with the brain tissue; and the implantable flexible comb-shaped neural microelectrode can automatically form a needle-like structure under the surface tension force of a liquid, thereby greatly reducing the implantation footprint in the brain tissue;
(2) the flexible comb-shaped neural microelectrode of the present invention has a unique structure gradually changing from a filament structure to a mesh structure to a plane structure, thus improving the mechanical stability of the flexible electrode during a deformation process;
(3) the mechanical properties of the implantable flexible comb-shaped neural microelectrode of the present invention match with brain tissue, so that inflammatory responses in the brain are avoided, and electrophysiological signals can be stably tracked and measured in a multi-site manner for a long time;
(4) the mechanical strength of the implantable flexible comb-shaped neural microelectrode of the present invention can be significantly improved after solidifying by the solidifying material, once implanted into the brain, due to the good biocompatibility of the solidifying material with the brain, it causes no immune response in the brain; and moreover the solidified material has good water solubility, and can decompose and release the flexible electrode in brain tissue.

BRIEF DESCRIPTION OF THE DRAWINGS

FIG. 6 is a schematic view showing an implantable flexible comb-shaped neural microelectrode with a transversely changing mesh structure of the present invention;

FIG. 7 is a schematic view showing an implantable flexible comb-shaped neural microelectrode with a uniform mesh structure of the present invention;

FIG. 8(a) is a picture showing the structure of an implantable flexible comb-shaped neural microelectrode in water in Example 1 of the present invention;

FIG. 8(b) is a picture showing the structure of an implantable flexible comb-shaped neural microelectrode in air in Example 1 of the present invention;

FIG. 9(a) is a picture showing the structure of the implantable flexible comb-shaped neural microelectrode in water in Example 2 of the present invention;

FIG. 9(b) is a picture showing the structure of the implantable flexible comb-shaped neural microelectrode in air in Example 2 of the present invention;

FIG. 10(a) is a picture showing the solidified implantable flexible comb-shaped neural microelectrode in Example 5 of the present invention;

FIG. 10(b) is a picture showing the solidified implantable flexible comb-shaped neural microelectrode in Example 5 of the present invention;

FIG. 11 is a picture showing the implantation process of the solidified implantable flexible comb-shaped neural microelectrode in a mouse brain in Example 5 of the present invention;

wherein, 1—flexible substrate layer, 2—flexible insulation layer, 3—metal connection wire layer, 4—filament structure, 5—mesh structure, 6—plane structure, 7—bonding area, 8—electrode sites, 9—carrier, 10—positive photoresist, 11—aluminum layer, 12—flexible material, 13—metal layer.

DETAILED DESCRIPTION

To better illustrate the present invention and to facilitate understanding of the technical solutions of the present invention, the present invention will be further described in detail below. However, the following examples are merely illustrative of the present invention and are not intended to limit the scope of the present invention, which is defined by the claims.

Figure 1:
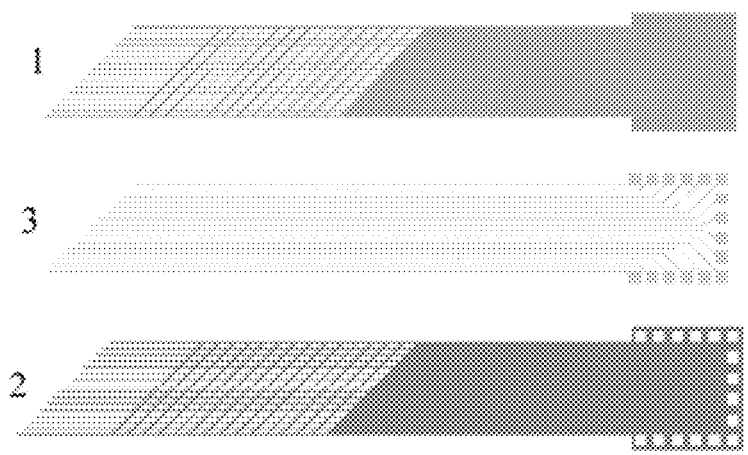
FIG. 1 is a schematic diagram showing the layered structure of an implantable flexible comb-shaped neural microelectrode of the present invention.

Specific examples of the present invention provide an implantable flexible comb-shaped neural microelectrode, which, as shown in FIG. 1, is mainly composed of a flexible substrate layer 1, a flexible insulation layer 2, and a metal connection wire layer 3 arranged between the flexible substrate layer and the flexible insulation layer.

Figure 2:
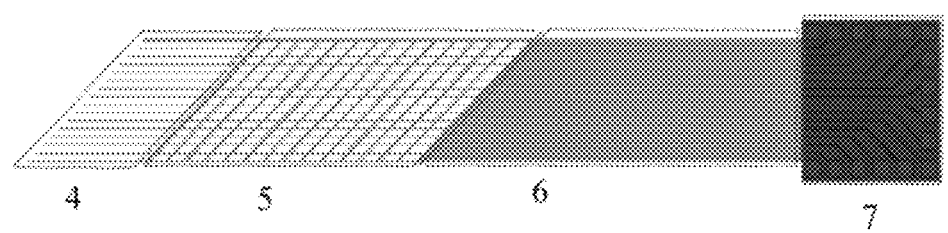
FIG. 2 is a schematic view showing the overall structure of an implantable flexible comb-shaped neural microelectrode of the present invention.
Figures 3A, 3B:
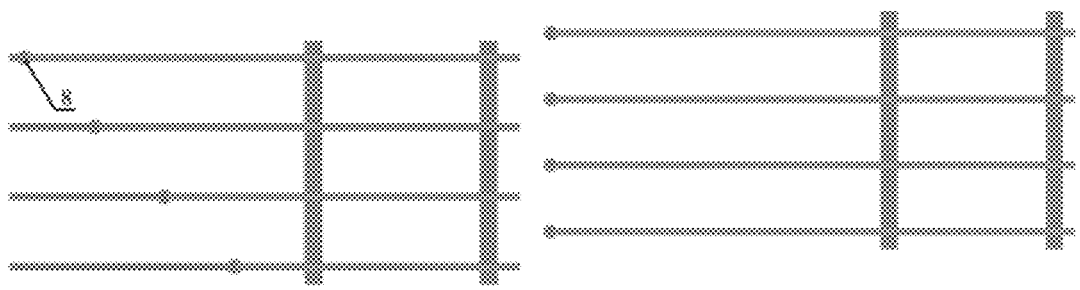
FIG. 3(a) is a schematic view showing the transversely distributed electrode sites on the filament structure of an implantable flexible comb-shaped neural microelectrode of the present invention.
FIG. 3(b) is a schematic view showing the aligned electrode sites on the filament structure of an implantable flexible comb-shaped neural microelectrode of the present invention.

As shown in FIG. 2, the flexible comb-shaped neural microelectrode comprises a filament structure 4, a mesh structure 5, a plane structure 6, and a bonding area 7 connected in sequence; electrode sites 8 are arranged on the filament structure 4 (as shown in FIG. 3(a) and FIG. 3(b)); and bonding pads are arranged on the bonding area 7.

The metal connection wire layer consists of metal connection wires connecting the electrode sites and the bonding pads.

There is no flexible insulation layer arranged on the surfaces of the electrode sites and the bonding pads.

Figure 4:
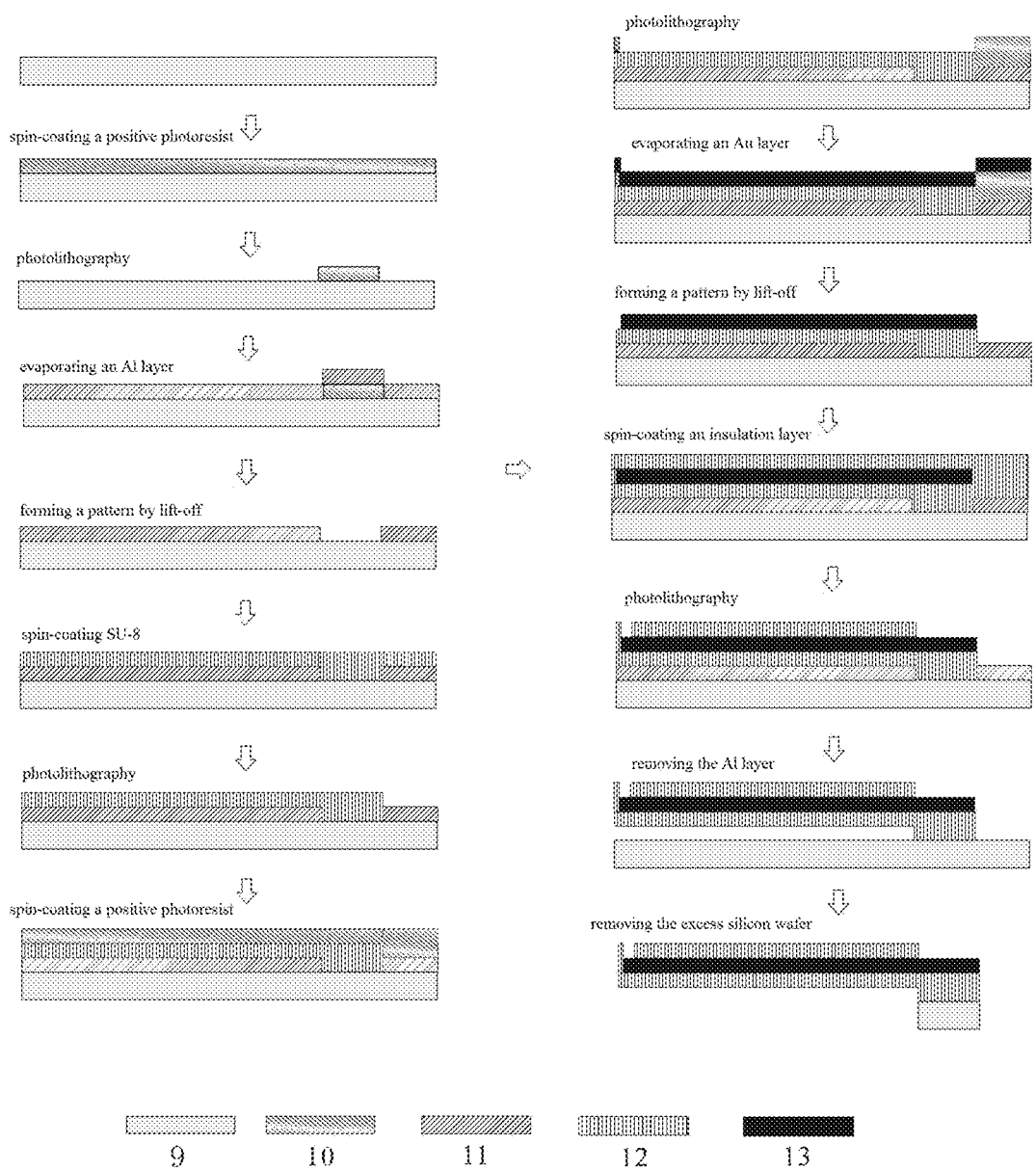
FIG. 4 is a process flow diagram of the preparation method of an implantable flexible comb-shaped neural microelectrode of the present invention.

Specific examples of the present invention provide a preparation method of the implantable flexible comb-shaped neural microelectrode, which, as shown in FIG. 4, comprises the following steps:

(1) a positive photoresist was spin-coated on a carrier, followed by prebaking, photolithography, leaving the bonding pad area protected by a photoresist, post-exposure baking to harden, and then removing the exposed photoresist;

(2) a sacrificial layer was evaporated or sputtered on the carrier obtained after the treatment of step (1), and a sacrificial layer and a marker pattern were formed after a lift-off process;

(3) a flexible substrate material was spin-coated on the side of the carrier where the sacrificial layer and the marker pattern were formed in step (2), a flexible substrate layer was formed by sequentially prebaking, exposing, post-exposure baking, and developing, and then hardened at a high temperature of 180° C.;

(4) a positive photoresist was spin-coated on the flexible substrate layer formed in step (3), patterned electrode sites, connection wires and bonding pads were formed by prebaking, exposing, and developing, and then an adhesive layer was formed by electron beam or thermal evaporation;

(5) a metal layer was formed by electron beam or thermal evaporation on the adhesive layer formed in step (4), and then electrode sites, connection wires, and bonding pads were produced after a lift-off process;

(6) a flexible insulation material was spin-coated on the metal layer where the electrode sites, connection wires, and bonding pads were formed in step (5), the electrode sites and the bonding pads were exposed by prebaking, exposing, post-exposure baking, and developing, and hardened at a high temperature of 180° C.;

(7) the flexible comb-shaped microelectrode obtained in step (6) was placed in a sacrificial layer removing solution, and the flexible comb-shaped microelectrode was released;

(8) the flexible comb-shaped microelectrode obtained in step (7) was cut to obtain a final product.

Specific examples of the present invention provide an implantation method of the implantable flexible comb-shaped neural microelectrode, comprising the following steps:

(1) the filaments of the flexible comb-shaped neural microelectrode spontaneously form a needle-like structure under the surface tension force of a liquid (such as water);

(2) the flexible comb-shaped neural microelectrode comb in step (1) was solidified with a solidifying material;

(3) the interface between the solidified flexible comb-shaped neural microelectrode and the carrier was solidified with an epoxy resin glue;

(4) the flexible comb-shaped neural microelectrode as treated in step (2) was inserted into a biological tissue, the portion not implanted in the biological tissue was washed to complete the implantation process.

The following are typical but non-limitative examples of the present invention:

Example 1

This example provides an implantable flexible comb-shaped neural microelectrode, which was mainly composed of a flexible substrate layer 1, a flexible insulation layer 2, and a metal Au connection wire layer 3 arranged between the flexible substrate layer 1 and the flexible insulation layer 2. Both the flexible substrate layer 1 and the flexible insulation layer 2 were made of SU-8 photoresist, and had a thickness of 5 µm. The metal Au connection wire layer 3 had a thickness of 100 nm.

The flexible comb-shaped neural microelectrode comprised a filament structure 4, a mesh structure 5, a plane structure 6, and a bonding area 7 connected in sequence; electrode sites 8 were arranged on the filament structure 4; and bonding pads were arranged on the bonding area 7.

The metal Au connection wire layer 3 was composed of metal Au connection wires having a wire width of 10 µm connecting the electrode sites 8 and the bonding pads; there was no flexible insulation layer 2 arranged on the surfaces of the electrode sites 8 and the bonding pads; and an adhesive layer was arranged between the flexible substrate layer 1 and the metal connection wire layer 3.

The electrode sites 8 were arranged on each filament of the filament structure 4, and there were a total of 16 electrode sites, which made up a periodic electrode array, as shown in FIG. 3(*b*).

The electrode sites 8 comprised electrode substrates and electrodes located at the center of the electrode substrates, wherein the electrode substrates were circular having a diameter of 40 µm, and the electrodes were circular having a diameter of 20 µm.

The overall length of the filament structure 4, the mesh structure 5, and the plane structure 6 in the flexible comb-shaped neural microelectrode was 1 cm, wherein the filament structure 4 had a length of 3 mm with the width of each filament being 20 µm; the plane structure 6 had a length of 0.5 cm and a width of 3 mm; each longitudinal support strip of the mesh structure 5 had a width of 50 µm; the bonding area 7 had a size of 3.5 mm×4 mm and each bonding pad on the bonding area 7 had a size of 400 µm×400 µm.

Figure 5:
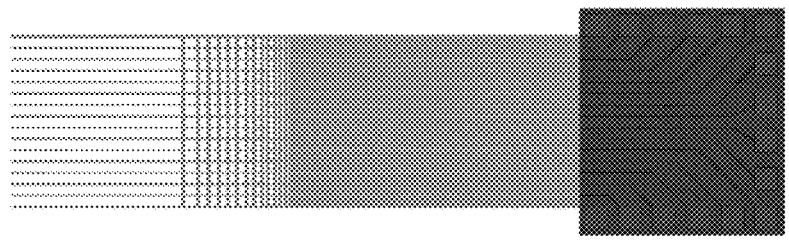
FIG. 5 is a schematic view showing an implantable flexible comb-shaped neural microelectrode with a longitudinally changing mesh structure of the present invention.

The mesh structure 5 was a longitudinally changing mesh structure, as shown in FIG. 5, which comprised transverse mesh strips and longitudinal support strips, wherein the distances between the adjacent longitudinal support strips increased gradually toward the side of the filament structure 4 in 10 µm increments.

The flexible comb-shaped neural microelectrode of this example could float on water, as shown in FIG. 8(*a*), and the filaments could form a needle-like structure under capillary force when withdrawn into air; and the mesh structure 5 could form a series of semi-puffs under the capillary force, as shown in FIG. 8(*b*).

The implantable flexible comb-shaped neural microelectrode of this example had a transition area between the filament and the external connection, wherein the mesh structure could form conformal contact with the brain in long-term, which could reduce the movement of the microelectrode relative to the brain tissue during use and greatly improve the performance of microelectrode; at the same time, the implantable flexible comb-shaped neural microelectrode had a unique filament-mesh-plane structure, which could form a needle-to-plane transition structure during deformation and effectively reduce tissue damage during the implantation process, so as to ensure the long-term stability of the microelectrode.

Example 2

This example provides a flexible comb-shaped neural microelectrode, which was mainly composed of a flexible substrate layer 1, a flexible insulation layer 2, and a metal platinum connection wire layer 3 arranged between the flexible substrate layer 1 and the flexible insulation layer 2. Both the flexible substrate layer 1 and the flexible insulation layer 2 were made of SU-8, and had a thickness of 5 µm. The metal platinum connection wire layer 3 had a thickness of 100 nm.

The flexible comb-shaped neural microelectrode comprised a filament structure 4, a mesh structure 5, a plane structure 6, and a bonding area 7 connected in sequence; electrode sites 8 were arranged on the filament structure 4; and bonding pads were arranged on the bonding area 7.

The metal platinum connection wire layer 3 was composed of metal platinum connection wires with a wire width of 5 µm, and the metal platinum connection wires connected the electrode sites 8 and the bonding pads; there was no flexible insulation layer 2 arranged on the surfaces of the electrode sites 8 and the bonding pads; and an adhesive layer was arranged between the flexible substrate layer 1 and the metal connection wire layer 3.

The electrode sites 8 were arranged on each filament of the filament structure 4, and there were a total of 16 electrode sites, which made up an electrode array, as shown in FIG. 3(*a*).

The electrode sites 8 comprised electrode substrates and electrodes located at the center of the electrode substrates, wherein the electrode substrates were circular having a diameter of 40 µm, and the electrodes were circular having a diameter of 20 µm.

The overall length of the filament structure 4, the mesh structure 5, and the plane structure 6 in the flexible comb-shaped neural microelectrode was 2 cm, wherein the filament structure 4 had a length of 3 mm with the width of each filament being 20 µm; the plane structure 6 had a length of 1 cm and a width of 3 mm; the longitudinal support strips in the mesh structure 5 had a width of 50 µm; the bonding area 7 had a size of 3.5 mm×4 mm and the bonding pad on the bonding area 7 had a size of 400 µm×400 µm.

The mesh structure 5 was a uniform mesh structure, as shown in FIG. 7, which comprised transverse mesh strips and longitudinal support strips, wherein the distances between the adjacent transverse mesh strips were 200 µm and the distances between the adjacent longitudinal support strips were 500 µm.

The flexible comb-shaped neural microelectrode of this example could float on water, as shown in FIG. 9(*a*), and the filaments could form a needle-like structure under the capillary force when withdrawn into air; and the mesh structure could form a series of semi-puffs under the capillary force, as shown in FIG. 9(*b*).

The implantable flexible comb-shaped neural microelectrode of this example had a transition area between the filament and the external connection, wherein the mesh structure could form conformal contact with the brain in long-term, which could reduce the movement of the microelectrode relative to the brain tissue during use and greatly improve the performance of microelectrode; at the same time, the implantable flexible comb-shaped neural microelectrode had a unique filament-mesh-plane structure, which could form a needle-to-plane transition structure during deformation and effectively reduce tissue damage during the implantation process, so as to ensure the long-term stability of the microelectrode.

Example 3

This example provides a flexible comb-shaped neural microelectrode, in which the flexible substrate layer 1 and the flexible insulation layer 2 were made of polyimide, the metal connection wires in the metal connecting wire layer 3 were made of iridium, both the flexible substrate layer 1 and the flexible insulation layer 2 had a thickness of 8 μm, the metal iridium connection wire layer had a thickness of 100 nm, the metal iridium connection wires had a width of 20 μm, the electrode substrates in the electrode sites 8 had a diameter of 50 μm, the electrodes in the electrode sites 8 had a diameter of 30 μm, the filament structure 4 had a length of 5 mm, with the width of each filament being 40 μm; the longitudinal support strips in the mesh structure 5 had a width of 100 μm, and the mesh structure 5 was a transversely changing mesh structure (as shown in FIG. 6), comprising transverse mesh strips and longitudinal support strips, and the distances between the adjacent transverse mesh strips gradually decreased to 30 μm toward the side of the plane structure 6, with the other structures being the same as those in Example 2.

The flexible comb-shaped neural microelectrode of this example could float on water, and could form into a needle-like structure under the capillary force when withdrawn into air; and the mesh structure could form a series of puffs and semi-puffs under the capillary force.

The implantable flexible comb-shaped neural microelectrode of this example had a transition area between the filament and the external connection, wherein the mesh structure could form contact interface with the brain in long-term, which could reduce the movement of the microelectrode relative to the brain tissue during use and greatly improve the performance of microelectrode; at the same time, the implantable flexible comb-shaped neural microelectrode had a unique filament-mesh-plane structure, which could form a needle-to-plane transition structure during deformation and effectively reduce tissue damage during the implantation process, so as to ensure the long-term stability of the microelectrode.

Example 4

This example provides a preparation method of the aforementioned flexible comb-shaped neural microelectrode, comprising the following steps:
(1) the carrier silicon wafer 9 was washed with acetone and water, oven dried, and then cleaned with an oxygen plasma process, a S1813 positive photoresist was spin-coated on the carrier silicon wafer 9, prebaked, and a marker pattern was formed by photolithography, leaving the bonding pad area protected by the photoresist, post-exposure baked to harden, and then oxygen plasma was used to remove the residual photoresist;
(2) a 100 nm aluminum layer was evaporated on the carrier 9 obtained after the treatment of the step (1) with electron beams, and a sacrificial aluminum layer and a marker pattern were formed after a lift-off process;
(3) a flexible material 12 was spin-coated on the side of the carrier where the sacrificial layer and the marker pattern were formed in step (2), followed by sequentially prebaking, exposing, post-exposure baking and developing to form a flexible substrate layer, which was then hardened at a high temperature of 180° C.;
(4) S1813 positive photoresist 10 was spin-coated on the flexible substrate layer formed in step (3), followed by prebaking, exposing, and developing to form patterned electrode sites, connection wires, and bonding pads, and then a 5 nm chromium adhesive layer was formed by thermal evaporation with electron beams;
(5) a metal layer 13 was formed by electron beam evaporation on the adhesive layer formed in step (4), and then electrode sites, connection wires, and bonding pads were produced after a lift-off process;
(6) a flexible material 12 was spin-coated on the metal layer 13 on which the electrode sites, connection wires, and bonding pads were formed in step (5), followed by prebaking, exposing, post-exposure baking, and developing to expose the electrode sites and the bonding pads, and a flexible insulation layer was prepared, and hardened at a high temperature of 180° C., then the aluminum sacrificial layer was removed by a ferric trichloride solution to release the flexible comb-shaped microelectrode.
(7) the flexible comb-shaped microelectrode obtained in step (6) was cut to obtain a final product.

Example 5

This example provides an implantation method of the aforementioned flexible comb-shaped neural microelectrode, comprising the following steps:
(1) a molten polyethylene glycol with a molecular weight of 2000 was coated on the flexible comb-shaped neural microelectrode for a solidifying treatment, so that the filament structure of the flexible comb-shaped neural microelectrode formed a needle-like shape;
(2) the interface between the solidified flexible comb-shaped neural microelectrode and the carrier was solidified with an epoxy resin glue;
(3) the flexible comb-shaped neural microelectrode formed in step (2) was inserted into brain tissue of a mouse, the portion not implanted in the brain tissue was rinsed with an artificial cerebrospinal fluid, and the implantation process was completed.

In this example, the structures of two solidified flexible comb-shaped neural microelectrodes were shown in FIG. 10(a) and FIG. 10(b), and their mechanical strength was remarkably increased. After implantation, polyethylene glycol causes no immune response in the brain because of its good biocompatibility with the brain; and polyethylene glycol can dissolve in the brain tissue because of its good solubility, and the flexible microelectrode can be released in the brain tissue. The implantation of a flexible comb-shaped neural electrode into a mouse brain was shown in FIG. 11.

Comparison Example 1

This comparison example provides a flexible neural microelectrode, whose components were substantially the same as those of the Example 2, with the exception of replacing the filament structure 4 with a plane structure, that is, having no filament structure.

Since the flexible neural microelectrode of this comparison example did not have a filament structure, it could not form a needle-like structure, and thus was liable to cause serious brain tissue damage during implantation.

Comparison Example 2

This comparison example provides a flexible neural microelectrode, whose components were substantially the same as those of the Example 2, with the exception of the lack of the mesh structure 5.

Due to the lack of the mesh structure, the flexible neural microelectrode of this comparison example had poor flexibility and formed poor contact to the brain surface, and was liable to move during use, and thus the electrode had low performance.

As can be seen from the combination of the results of Examples 1-5 and Comparison Examples 1-2, in contrast to conventional two-dimensional planar neural electrodes, the implantable flexible comb-shaped neural microelectrode of the present invention has electrode sites on each filament of the filament structure, and these electrode sites make up an electrode array, wherein each filament can move freely with the brain tissue; and the implantable flexible comb-shaped neural microelectrode can automatically form a needle-like structure under the surface tension force of a liquid, thereby greatly reducing the implantation footprint in the brain tissue; The flexible comb-shaped neural microelectrode has a unique structure that gradually changes from a filament to a mesh to plane, thus improving the mechanical stability of the flexible electrode during a deformation process.

The mechanical properties of the implantable flexible comb-shaped neural microelectrode match with that of the brain tissue, so that it will not induce an inflammatory response in the brain, and electrophysiological signals of the brain can be stably tracked and measured in a multi-site manner for a long time. The mechanical strength of the implantable flexible comb-shaped neural microelectrode can be significantly improved after solidified by the solidifying material, once implanted into the brain, due to the good biocompatibility of the solidifying material with the brain, it cause no immune response in the brain; and the solidified material has good water solubility, and can decompose and release the flexible electrode in brain tissue.

The applicant declares that the detailed methods of the present invention are described by the above-described embodiments, but the present invention is not limited to the above process steps, that is, it does not mean that the present invention must be implemented depending on the process steps described above. It will be apparent to those skilled in the art that any modifications of the present invention, equivalent substitutions of the materials for the product of the present invention, and additions of auxiliary ingredients, selections of the specific means and the like, are all within the protection and disclosure scopes of the present invention.

What is claimed is:

1. An implantable flexible comb-shaped neural microelectrode, comprising a flexible substrate layer (1), a flexible insulation layer (2), and a metal connection wire layer (3) arranged between the flexible substrate layer (1) and the flexible insulation layer (2);
   a filament structure (4), a mesh structure (5), a plane structure (6), and a bonding area (7) connected in sequence; electrode sites (8) are arranged on the filament structure (4); bonding pads are arranged on the bonding area (7);
   wherein the metal connection wire layer (3) comprises metal connection wires connecting the electrode sites and the bonding pads;
   wherein there is no flexible insulation layer (2) arranged on the surfaces of the electrode sites and the bonding pads.

2. The implantable flexible comb-shaped neural microelectrode according to claim 1, wherein at least one electrode site (8) is arranged on each filament of the filament structure (4).

3. The implantable flexible comb-shaped neural microelectrode according to claim 1, wherein the mesh structure (5) is any one selected from the group consisting of a longitudinally changing mesh structure, a transversely changing mesh structure, a uniform mesh structure, and a mesh structure with a longitudinal angle of 45 degrees, or a combination of at least two selected therefrom,
   wherein the longitudinally changing mesh structure comprises transverse mesh strips and longitudinal support strips, and the distances between the adjacent longitudinal support strips increase gradually toward the side of the filament structure (4),
   wherein the transversely changing mesh structure comprises transverse mesh strips and longitudinal support strips, and the widths of the transverse mesh strips gradually decrease from the plane structure (6) to the filament structure (4), and,
   wherein the uniform mesh structure comprises transverse mesh strips and longitudinal support strips and the distances between the adjacent transverse mesh strips are equal.

4. The implantable flexible comb-shaped neural microelectrode according to claim 1, the filament structure (4) has 1 to 1000 filaments, each filament has 1 to 1000 electrode sites (8).

5. The implantable flexible comb-shaped neural microelectrode according to claim 1, wherein each of the electrode sites (8) comprises an electrode substrate and an electrode located at the center of the electrode substrates.

6. The implantable flexible comb-shaped neural microelectrode according to claim 1, wherein the flexible substrate layer (1) is any one selected from the group consisting of SU-8 photoresist, parylene, and polyimide, or a combination of at least two selected therefrom.

7. The implantable flexible comb-shaped neural microelectrode according to claim 1, wherein the flexible insulation layer (2) is any one selected from the group consisting of SU-8 photoresist, parylene, and polyimide, or a combination of at least two selected therefrom.

8. The implantable flexible comb-shaped neural microelectrode according to claim 1, wherein the metal connection wire layer (3) is any one selected from the group consisting of gold, platinum, and iridium, or a combination of at least two selected therefrom.

9. The implantable flexible comb-shaped neural microelectrode according to claim 1, wherein the overall length of the filament structure (4), the mesh structure (5), and the plane structure (6) is 1 mm to 5 cm.

10. The implantable flexible comb-shaped neural microelectrode according to claim 1, wherein the filament structure (4) has a length of 1 mm to 5 cm, and each filament in the filament structure (4) has a width of 1 μm to 200 μm.

11. A preparation method of the implantable flexible comb-shaped neural microelectrode according to claim 1, comprising at least one of the following steps:
    (11-1) spin-coating a positive photoresist on a carrier, prebaking, photolithography to generate marker patterns for the arrangement of a flexible substrate layer, a flexible insulation layer, and a metal connection wire layer of the implantable flexible comb-shaped neural microelectrode, leaving the bonding pad area protected by a photoresist, post-exposure baking to harden, and removing the exposed photoresist;

(11-2) evaporating or sputtering a sacrificial layer on the carrier obtained after the treatment of step (11-1), and forming a sacrificial layer that can be removed to enable the releasing of the implantable flexible comb-shaped neural microelectrode and marker patterns after a lift-off process;

(11-3) spin-coating a flexible substrate material on the side of the carrier where the sacrificial layer and the marker pattern patterns are formed in step (11-2), sequentially prebaking, exposing, post-exposure baking, and developing to form a flexible substrate layer, and hardening at a high temperature of 180° C.;

(11-4) spin-coating a positive photoresist on the flexible substrate layer formed in step (11-3), prebaking, exposing, and developing to form patterned electrode sites, connection wires, and bonding pads, and then forming an adhesive layer by electron beam or thermal evaporation;

(11-5) forming a metal layer by electron beam or thermal evaporation on the adhesive layer formed in step (11-4), and then forming electrode sites, connection wires, and bonding pads after a lift-off process;

(11-6) spin-coating a flexible insulation material on the metal layer where the electrode sites, connection wires, and bonding pads are formed in step (11-5), prebaking, exposing, post-exposure baking, and developing to expose the electrode sites and the bonding pads, and hardening at a high temperature of 180° C.;

(11-7) placing the flexible comb-shaped microelectrode obtained in step (11-6) in a sacrificial layer removing solution, and releasing the flexible comb-shaped microelectrode;

(11-8) cutting the flexible comb-shaped microelectrode obtained in step (11-7) to obtain the implantable flexible comb-shaped neural microelectrode according to claim 1.

12. The preparation method according to claim 11, wherein the carrier on which the positive photoresist is spin-coated in step (11-1) is pretreated, and the pretreatment consists of: washing the carrier with acetone and water, oven drying, and then cleaning with an oxygen plasma process, wherein the carrier is a silicon wafer and/or a glass substrate.

13. The preparation method according to claim 11, in which the sacrificial layer in step (11-2) is an aluminum layer and/or a nickel layer.

14. A use method of the implantable flexible comb-shaped neural microelectrode according to claim 1, comprising at least one of the following steps:

(14-1) withdrawing the implantable flexible comb-shaped neural microelectrode from liquid into air, so that the filaments of the flexible comb-shaped neural microelectrode spontaneously form a needle-like structure under the surface tension force of a liquid;

(14-2) solidifying the flexible comb-shaped neural microelectrode in step (14-1) with a solidifying material;

(14-3) solidifying the interface between the solidified flexible comb-shaped neural microelectrode and the carrier with an epoxy resin glue;

(14-4) inserting the flexible neural microelectrode as treated in step (14-2) into a biological tissue, washing the portion that is not implanted in the biological tissue to complete the implantation process.

15. The use method according to claim 14, in which the solidifying material in step (2) is polyethylene glycol.

16. The use method according to claim 14, in which the solidifying in step (14-2) consists of: coating the molten solidifying material on the flexible comb-shaped neural microelectrode for solidifying.

17. The use method according to claim 14, in which the washing in step (14-4) consists of: washing with an artificial cerebrospinal fluid.

* * * * *